United States Patent [19]

Herbstman et al.

[11] Patent Number: 5,393,914
[45] Date of Patent: Feb. 28, 1995

[54] MOTOR FUEL DETERGENT ADDITIVES-HYDROCARBYLOX-YPOLYETHER ALLOPHONATE ESTERS OF 2-HYDROXY ETHANE

[75] Inventors: Sheldon Herbstman, New City; Cadorette, Constance A., Newburgh, both of N.Y.

[73] Assignee: Texaco Inc., White Plains, N.Y.

[21] Appl. No.: 938,808

[22] Filed: Sep. 1, 1992

[51] Int. Cl.$^6$ ............................................. C07C 229/00
[52] U.S. Cl. ......................................... 560/29; 560/34
[58] Field of Search ................................... 560/34, 29

[56] References Cited

U.S. PATENT DOCUMENTS

| | | | |
|---|---|---|---|
| 4,191,527 | 3/1990 | Lewis et al. | 44/71 |
| 4,288,612 | 9/1981 | Lewis et al. | 560/159 |
| 4,326,020 | 11/1980 | Lewis et ala. | 560/159 |
| 4,389,401 | 6/1983 | Smolanoff | 560/34 |
| 4,755,312 | 7/1988 | Wollenberg | 252/51.5 |
| 4,881,945 | 11/1989 | Buckley, III | 44/62 |
| 5,084,195 | 1/1992 | Camenzind, et al. | 252/47.5 |
| 5,103,041 | 4/1992 | A'Court, et al. | 560/132 |

*Primary Examiner*—C. Warren Ivy
*Assistant Examiner*—Raymond Covington
*Attorney, Agent, or Firm*—Christopher Nicastri; George J. Darsa

[57] ABSTRACT

The present invention provides a novel class of compounds, useful as gasoline detergent additives, comprising hydrocarbyloxypolyether allophonate esters of 2-hydroxy ethane. The present invention also provides a motor fuel composition containing the novel allophonate esters and further provides a method of synthesizing the allophonate esters of the present invention.

6 Claims, No Drawings

MOTOR FUEL DETERGENT ADDITIVES-HYDROCARBYLOXYPOLYETHER ALLOPHONATE ESTERS OF 2-HYDROXY ETHANE

BACKGROUND OF THE INVENTION

1. Field of the Invention

This invention is related to gasoline engine cleaners and detergents, and more particularly to gasoline intake valve deposit (IVD) inhibitor additives, i.e., agents which assist in preventing and removing deposits from intake valves and related parts of a gasoline combustion engine. This invention also relates to combustion chamber deposit inhibitors, which reduce combustion chamber deposits, resulting in lower octane requirement increase and lower $NO_x$ emissions.

2. Description of Related Information

Combustion of a hydrocarbon motor fuel in an internal combustion engine generally results in the formation and accumulation of deposits on various parts of the combustion chamber as well as in the fuel intake and on the exhaust systems of the engine. The presence of deposits in the combustion chamber seriously reduces the operating efficiency of the engine. First, deposit accumulation within the combustion chamber inhibits heat transfer between the chamber and the engine cooling system. This leads to higher temperatures within the combustion chamber, resulting in increases in the end gas temperature of the incoming charge. Consequently, end gas auto-ignition occurs causing engine knock. In addition, the accumulation of deposits within the combustion chamber reduces the volume of the combustion zone, causing a higher than design compression ratio in the engine. This, in turn, can also lead to engine knocking. A knocking engine does not effectively utilize the energy of combustion. Moreover, a prolonged period of engine knocking can cause stress fatigue and wear in pistons, connecting rods, bearings and cam rods of the engine. The phenomenon noted is characteristic of gasoline powered internal combustion engines. It may be overcome by employing a higher octane gasoline which resists knocking for powering the engine. This need for a higher octane gasoline as mileage accumulates has become known as the engine octane requirement increase (ORI) phenomenon. It is particularly advantageous if engine ORI can be substantially reduced or eliminated by preventing or modifying deposit formation in the combustion chambers of the engine.

Another problem common to internal combustion engines is the formation of intake valve deposits, which is an especially serious problem. Intake valve deposits interfere with valve closing and eventually result in poor fuel economy. Such deposits interfere with valve motion and valve sealing, cause valve sticking, and, in addition, reduce volumetric efficiency of the engine and limit maximum power. Valve deposits are produced from the combustion of thermally and oxidatively unstable fuel or lubricating oil oxidation products. The hard carbonaceous deposits produced collect in the tubes and runners that are part of the exhaust gas recirculation (EGR) flow. These deposits are believed to be formed from exhaust particles which are subjected to rapid cooling while mixing with the air-fuel mixture. Reduced EGR flow can result in engine knock and in increased $NO_x$ emissions. It would therefore be desirable to provide a motor fuel composition which minimizes or overcomes the formation of intake valve deposits and subsequent valve sticking problems.

There are additives on the market which assist in the removal of deposits, particularly on the intake valves, such as OGA-472 TM, a product of the Oronite Co. of Wilmington, Del. These additives lack sufficient deposit cleanup activity, however, and their efficacy can be improved upon. In addition, polyisobutylene (PIB) based detergents tend to cause octane requirement increase.

Thus, it is an object of the present invention to provide a gasoline additive which will effectively remove deposits from, and prevent the formation of deposits on, the intake valves of a gasoline spark ignition engine. It is another object of the present invention to provide a gasoline additive which will perform this function without contributing to the buildup of combustion chamber deposits and, therefore, without causing octane requirement increase.

SUMMARY OF THE INVENTION

The present invention provides a novel class of compounds, useful as gasoline detergent additives, comprising hydrocarbyloxypolyether allophonate esters of 2-hydroxy ethane. These novel allophonate esters can be represented by the formula:

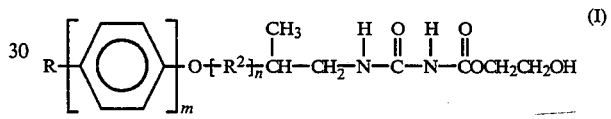

where R is a $C_9$-$C_{25}$ alkyl group, $R^2$ is a $C_2$ to $C_4$ oxyalkylene group, m is 0 or 1, and n is a number between about 5 and about 30.

The present invention also provides a motor fuel composition comprising:
(a) a major portion of a hydrocarbon fuel boiling in the range between 90° F. and 370° F.; and
(b) a minor amount, sufficient to reduce the formation of deposits on intake valves, of the hydrocarbyloxypolyether allophonate ester of 2-hydroxy ethane of FIG. 1.

A method of synthesizing the allophonate esters of the present invention is also provided.

DETAILED DESCRIPTION OF THE INVENTION

Applicant's have discovered a new class of allophonate esters which are useful as detergents in motor fuel compositions. These allophonate ester detergents are more efficacious in removing and preventing the build up of deposits on intake valves than some commercially available detergent packages. In addition, the allophonate ester motor fuel additives of the present invention will not contribute significantly, if at all, to octane requirement increase, a problem which confronts all gasoline spark ignition engines.

The allophonate esters of the present invention are represented by the formula:

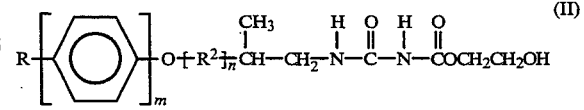

where R is a $C_9$–$C_{25}$ alkyl group, $R^2$ is a $C_2$ to $C_4$ oxyalkylene group, m is 0 or 1, and n is a number between about 5 and about 30. In Figure II, the R group is shown located in the para position. It is probable that the R group will sometimes be located in the ortho position, and the allophonate esters of the present invention therefore include mixtures of both the para and ortho isomers. The formula of Figure II is hereinafter intended to represent both the para and ortho isomers and mixtures thereof.

Preferably, R is a $C_9$ to $C_{21}$ alkyl group, $R^2$ is an oxypropylene group, m=1, and n is a number between about 9 and about 15. In another preferred embodiment, R is a $C_{12}$ to $C_{21}$ alkyl group, $R^2$ is an oxypropylene group, m=0, and n is a number between about 9 and about 15

More preferably, R is a nonyl group, $R^2$ is an oxypropylene group, m=1, and n is about 12. This more preferred allophonate ester can be represented by the formula:

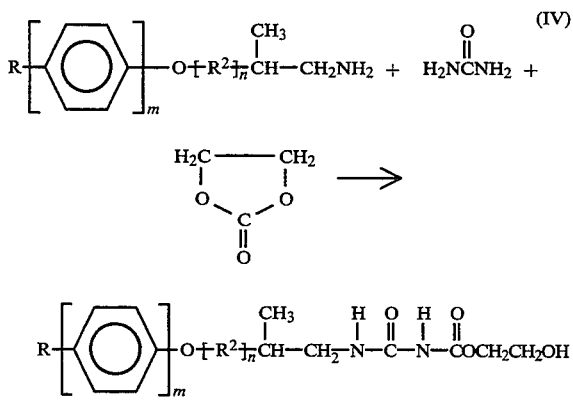

It should be noted that the phenyl ring can contain a second nonyl substituent. In such cases the first nonyl group would be in the para position and the second nonyl group would be in the ortho position to the remainder of the molecule.

Synthesis of Allophonate Esters

The allophonate esters of the present invention are the product of the reaction of a hydrocarbyloxypolyoxyalkylene amine with urea and ethylene carbonate:

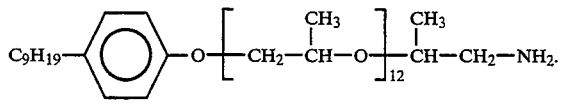

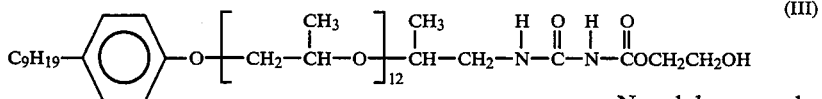

where R is a $C_9$–$C_{25}$ alkyl group, $R^2$ is a $C_2$ to $C_4$ oxalkylene group, m is 0 or 1, and n is a number between about 5 and about 30.

The polyetheramine reactants useful in the present invention can be represented by the formula:

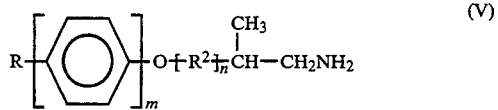

where R is a $C_9$–$C_{25}$ alkyl group, $R^2$ is a $C_2$ to $C_4$ oxalkylene group, m is 0 or 1, and n is a number between about 5 and about 30. The R group can be located in the para or ortho position.

Preferably, R is a $C_9$ to $C_{21}$ alkyl group, $R^2$ is an oxypropylene group, m=1, and n is a number between about 9 and about 15. In another preferred embodiment, R is a $C_{12}$ to $C_{21}$ alkyl group, $R^2$ is an oxypropylene group, m=0, and n is a number between about 9 and about 15.

The most preferred polyetheramine, nonylphenoxypolyoxypropyleneamine, can be represented by the formula:

Nonylphenoxypolyoxypropyleneamine is available from Texaco Chemical Company. It should be noted that the polyetheramines useful in the present invention can have two nonyl groups substituted onto the phenyl ring. In fact, it is likely that commercially available nonylphenoxypolyoxypropyleneamine contains at least some of the di-nonyl substituted phenyl ring versions of this compound. In such cases, the second nonyl group is located in the ortho position relative to the bulk of the molecule.

Ethylene carbonate is commercially available from the Texaco Chemical Company.

The allophonate esters of the present invention can be prepared via the following reaction. In step one a polyetheramine is heated with urea at a temperature of about 130° C. for about 6–15 (preferably about 6) hours with stirring, under a nitrogen sparge to remove the evolved ammonia. After cooling, the mixture is filtered free of unreacted urea. The cooling and filtering steps are optional.

In step two, the polyether urea product of step one is reacted with ethylene carbonate at a temperature of about 130° C. for about 1–15 (preferably about 3) hours with stirring. The reaction mixture is filtered free of unreacted reactants, and stripped under vacuum at about 80° C. for about an hour. The product is an allophonate ester of the present invention.

The synthesis can also be performed in reverse order, i.e., the ethylene carbonate can be reacted with urea in the first step and the product of this first reaction can then be reacted with the polyether amine in the second step.

All of the reactions described above can be conducted in solution in hydrocarbon type heavy oils (e.g., SNO-600, SNO-850, etc.) Preferably, the reactants are employed in the stoichiometric amount, i.e., 1:1:1.

The Motor Fuel Composition

The motor fuel composition of the present invention comprises a major portion of a hydrocarbon fuel boiling in the gasoline range between 90° F. and about 370° F., and a minor portion of the allophonate ester additive of the present invention sufficient to reduce the formation of deposits on intake valves.

Preferred base motor fuel compositions are those intended for use in spark ignition internal combustion engines. Such motor fuel compositions, generally referred to as gasoline base stocks, preferably comprise a mixture of hydrocarbons boiling in the gasoline boiling range, preferably from about 90° F. to about 370° F. This base fuel may consist of straight chain or branched chain paraffins, cycloparaffins, olefins, aromatic hydrocarbons, or mixtures thereof. The base fuel can be derived from, among others, straight run naphtha, polymer gasoline, natural gasoline, or from catalytically cracked or thermally cracked hydrocarbons and catalytically reformed stock. The composition and octane level of the base fuel are not critical and any conventional motor fuel base can be employed in the practice of this invention. In addition, the motor fuel composition may contain any of the additives generally employed in gasoline. Thus, the fuel composition can contain anti-knock compounds such as tetraethyl lead compounds, anti-icing additives, and the like.

In a broad embodiment of the fuel composition of the present invention, the concentration of the additive is about 25 to about 125 PTB (pounds per thousand barrels of gasoline base stock). In a preferred embodiment, the concentration of the additive composition is about 50 to about 125 PTB. In a more preferred embodiment, the concentration of the additive composition is about 80–100 PTB.

The additive of the present invention can also be used effectively with heavy oils such as SNO-600, SNO-850, etc., or with synthetics such as polypropylene glycol (1000 m.w.), at concentrations of 30–100 PTB, and 65 PTB in particular.

The additive of the present invention is effective in very small concentrations and, therefore, for consumer end use it is desirable to package it in dilute form. Thus, a dilute form of the additive composition of the present invention can be provided comprising a diluent e.g., xylene and about 1 to about 50 wt. % of the additive.

The preparation and advantages of the allophonate esters of the present invention are further illustrated by the following examples.

EXAMPLE 1

Preparation of N-nonylphenoxypolypropoxy Allophonate Ester of 2-Hydroxy Ethane 200 g (0.2 mole) of polyetheramine with molecular weight of about 1000 was reacted with 19.8 g (0.33 mole) urea at 130° C. for 2 hours. After 2 hours, 26.4 g (0.3 mole) of ethylene carbonate was introduced at 130° C. and reacted at this temperature an additional 6 hours. The reaction product was filtered hot and then vacuum stripped at 80° C. for 2 hours. The final clear product weighed 204.7 grams. It had the following analysis:

Nitrogen 3.50 wt %
TBN 12.78

Molecular weight (by Gel Phase Chromatography) 990

The structure, see Figure I, was confirmed by infrared spectroscopy and nuclear magnetic resonance.

EXAMPLE 2

Intake Valve Keep Clean Test

The motor fuel composition of the present invention is advantageous in that it reduces intake valve deposit formation. The advantage of the instant invention in controlling intake valve deposit formation has been shown by the comparison of the performance of motor fuel compositions of the present invention and a motor fuel containing a commercially available detergent package.

The following fuel compositions were subjected to Honda Generator - IVD "Keep Clean" testing. Fuel A contained 100 PTB of the product of Example 1 as a detergent additive and Fuel B contained 60 PTB of a commercially available gasoline additive package. The base fuel used in each fuel composition was a commercial unleaded fuel with 45% aromatics, 6% olefins, and the remainder paraffins. The octane rating, calculated as the average of research and motor octane ratings was 87. Base fuel boiling point data is listed in Table I as follows:

TABLE I

| Base Fuel | |
|---|---|
| initial boiling point | 99° F. |
| 50% point | 253° F. |
| 90% point | 410° F. |
| end point | 415° F. |

The Honda Generator Test employed a Honda ES6500 generator with the following specifications:

TABLE II

| Honda ES6500 Generator | |
|---|---|
| Type: | 4-stroke, overhead cam, 2-cylinder |
| Cooling system: | Liquid-cooled |
| Displacement: | 369 cubic cm. (21.9 cu. in) |
| Bore × stroke: | 56 × 68 mm (2.3 × 2.7 in) |
| Maximum Horsepower: | 12.2 HP/3600 rpm |
| Maximum Torque: | 240 kg-cm (17.3 ft-lb)/3000 rpm |

Each generator was equipped with an auto-throttle controller to maintain the rated speed when load was applied. Load was applied to each generator by plugging in a water heater. Various loads were simulated by changing the size of the water heaters connected to the generator.

The procedure for the Honda Generator Test is as follows. The test was started with a new or clean engine (clean valve, manifold, cylinder head, combustion chamber) and a new charge of lubricant. The generator was operated for 80 hours on the fuel to be tested following the test cycle of 2 hours at 1500 Watt load and 2 hours at 2500 Watt load, both at 3600 r.p.m. The engine was thereafter disassembled and the cylinder head stored, with valve spring and seal removed, in a freezer overnight at 0° F.

IV Stickiness Test

A trained rater quantified the effort to push open the intake valves by hand. The amount of effort was correlated to valve sticking problems in vehicles: i.e., valves that could not be pushed open by hand generally correlated with cold starting problems in vehicles.

CRC IV Test

The intake system components (valve, manifold, cylinder head) and combustion chamber were rated visually according to standard Coordinating Research Council (CRC) procedures (scale from 1–10:1=dirty; 10=clean). The performance of the test fuel was measured in part by the cleanliness of the intake system components.

Fuels A and B were subjected to the Honda Generator intake valve keep clean test procedure. The results are summarized in Table III:

TABLE III

| FUEL | CRC IV | Wt., mg., IV | IV Stickiness |
|------|--------|--------------|---------------|
| A    | 9.6    | 0.013        | No            |
| B    | 6.03   | 0.269        | No            |

The additive gasoline of the present invention, Fuel A, demonstrated excellent CRC valve ratings, virtually no deposits on the intake valves (13 mg or less) and exhibited no stickiness. The fuel containing the commercially available additive package showed a poor CRC rating and gave 269 mg intake valve deposits. Therefore the allophonate ester of the present invention demonstrates excellent detergency and intake valve detergency keep clean properties.

EXAMPLE 6

Thermal Gravimetric Analysis (TGA)

A sample of the allophonate ester of Example 1 was analyzed for rate of thermal decomposition using TGA analysis, in order to determine whether they will increase combustion chamber deposits. The procedure used was the Chevron test method, which involves heating the additive compound in air at a rapid rate and measuring its volatility at 200° C. and 295° C. The test method is more specifically described as follows:

The sample is heated to 200° C., kept at this temperature for 30 minutes, and then heated to 295° C., where it is kept for an additional 30 minutes. The weight of the sample, (initially about 20 mg) is recorded at the start, after the first heating period and after the final heating period. The difference in weights from the start to 200° C., and from 200° C. to 295 ° C. is recorded and the percent loss, i.e., volatility, is calculated. (The final weight at 295° C. is also considered residue.) The heating is done under a flow of air at 60 cc/min.

The following results were obtained:

TABLE IV

| Run | Additive | % Volatilized (in Air) 200° C. | % Volatilized (in Air) 295° C. | Residue (wt. %) 295° C. |
|-----|----------|------|------|------|
| 1 | Product of Example 1- N-nonylphenoxypoly- isopropoxy allophonate ester of 2-hydroxy ethane | 15 | 90 | 10 |
| 2 | OGA-472 ™ | 34.5 | 62.8 | 37.2 |

The test results for runs 1 and 2 show that at 295 ° C., 90% of the additive of the present invention had thermally decomposed and volatilized, compared to only 62.8% for a PIB containing derivative such as OGA-472 ™. These results indicate that the additives of the present invention should leave only small amounts of combustion chamber deposits during the actual engine operation, and therefore will not contribute to octane requirement increase.

We claim:

1. An allophonate ester comprising a compound of formula

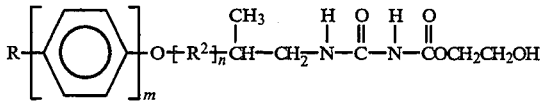

where R is a $C_9$–$C_{25}$ alkyl group, $R^2$ is a $C_2$ to $C_4$ oxyalkylene group, m is 0 or 1, and n is a number between about 5 and about 30.

2. The allophonate ester of claim 1 where R is a $C_9$ to $C_{21}$ alkyl group, and m=1.

3. The allophonate ester of claim 1 where R is a $C_{12}$ to $C_{21}$ alkyl group and m=0.

4. The allophonate ester of claim 1 where $R^2$ is an oxypropylene group.

5. The allophonate ester of claim 1 where n is a number between about 9 and about 15.

6. The allophonate ester of claim 1 where R is a nonyl group, $R^2$ is an oxypropylene group, m is 1 and n is about 12.

* * * * *